US010434256B2

(12) United States Patent
Ettlin et al.

(10) Patent No.: US 10,434,256 B2
(45) Date of Patent: Oct. 8, 2019

(54) SYRINGE

(71) Applicant: Sulzer Mixpac AG, Haag (CH)

(72) Inventors: Josef Ettlin, Eichberg (CH); Marco Zünd, Widnau (CH)

(73) Assignee: SULZER MIXPAC AG, Haag (CH)

( * ) Notice: Subject to any disclaimer, the term of this patent is extended or adjusted under 35 U.S.C. 154(b) by 155 days.

(21) Appl. No.: 15/117,648

(22) PCT Filed: Feb. 10, 2015

(86) PCT No.: PCT/EP2015/052685
§ 371 (c)(1),
(2) Date: Aug. 9, 2016

(87) PCT Pub. No.: WO2015/121213
PCT Pub. Date: Aug. 20, 2015

(65) Prior Publication Data
US 2016/0354545 A1 Dec. 8, 2016

(30) Foreign Application Priority Data

Feb. 11, 2014 (EP) .................................... 14154732

(51) Int. Cl.
*A61M 5/19* (2006.01)
*A61M 5/28* (2006.01)
(Continued)

(52) U.S. Cl.
CPC ............ *A61M 5/19* (2013.01); *A61M 5/2033* (2013.01); *A61M 5/283* (2013.01); *A61M 5/284* (2013.01);
(Continued)

(58) Field of Classification Search
CPC .. A61M 5/19; A61M 5/31596; A61M 5/3202; A61M 5/322; A61M 5/284; A61M 5/283; A61M 5/288; A61M 2005/1787
See application file for complete search history.

(56) References Cited

U.S. PATENT DOCUMENTS 4,171,698 A * 10/1979 Genese ................. A61M 5/284
604/88
4,767,413 A 8/1988 Haber et al.
(Continued)

FOREIGN PATENT DOCUMENTS

CN 88102077 A 10/1988
CN 1065800 A 11/1992
(Continued)

OTHER PUBLICATIONS

International Search Report dated May 21, 2015 in International Application No. PCT/EP2015/052685, filed Feb. 10, 2015.
(Continued)

*Primary Examiner* — Bradley J Osinski
(74) *Attorney, Agent, or Firm* — Global IP Counselors, LLP

(57) ABSTRACT

A syringe includes a hollow body, a piston and a seal. The hollow body has a surrounding hollow body surface and forms a passage therein. An axis is formed in an axial longitudinal direction of the hollow body and the passage has a rear body opening and a front body opening arranged opposite to one another in the longitudinal direction. A first needle seat is formed at the front body opening, in which a needle cannula is arranged and relative to which the needle cannula is movable along the axis. The piston is arranged in the hollow body and is movable in the passage along the axis. The seal is able to be cancelled such that a receiving (Continued)

chamber and a supply space of the syringe are in flow communication in a release position.

22 Claims, 8 Drawing Sheets

(51) Int. Cl.
    *A61M 5/32*     (2006.01)
    *A61M 5/20*     (2006.01)
    *A61M 5/315*     (2006.01)
    *A61M 5/178*     (2006.01)

(52) U.S. Cl.
    CPC ........ *A61M 5/288* (2013.01); *A61M 5/31596* (2013.01); *A61M 5/3202* (2013.01); *A61M 5/322* (2013.01); *A61M 5/3234* (2013.01); *A61M 2005/1787* (2013.01); *A61M 2005/3224* (2013.01)

(56) References Cited

U.S. PATENT DOCUMENTS

| | | | |
|---|---|---|---|
| 5,656,031 A * | 8/1997 | Thorne | A61M 5/283 604/110 |
| 6,981,963 B2 * | 1/2006 | Barker | A61M 5/326 604/191 |
| 2004/0116853 A1 * | 6/2004 | Halseth | A61M 5/283 604/110 |
| 2014/0170594 A1 * | 6/2014 | Larson | A61C 19/08 433/90 |

FOREIGN PATENT DOCUMENTS

| | | |
|---|---|---|
| CN | 201015668 Y | 2/2008 |
| WO | 9727890 A1 | 8/1997 |
| WO | 0145776 A1 | 6/2001 |
| WO | 020721711 A2 | 9/2002 |

OTHER PUBLICATIONS

International Preliminary Report on Patentability and Written Opinion dated Aug. 16, 2016 in International Application No. PCT/EP2015/052685, filed Feb. 10, 2015.

European Office Action dated Feb. 9, 2018 in corresponding EP Patent Application No. 15704991.7.

* cited by examiner

SYRINGE

CROSS-REFERENCE APPLICATION

This application is a U.S. National Stage Application of International Application No. PCT/EP2015/052685, filed Feb. 10, 2015, which claims priority to European Application No. 14154732.3, filed Feb. 11, 2014, the contents of each of which is hereby incorporated herein by reference.

BACKGROUND

Field of Invention

The invention relates to a syringe.

Background Information

Syringes having a needle cannula are already known. Syringes typically comprise a hollow body, a piston movable therein and a conical nozzle. There are furthermore versions having a screw thread at the nozzle to which the needle cannula or a hose can be connected. There are two-part syringes which only comprise the hollow body and a piston and there are three-part syringes which have a rubber plug at the lower end of the piston. With some syringes, for example insulin syringes, the needle cannula is bonded in. Syringes can comprise plastic, glass, metal and rubber. Syringes are equally known having a needle cannula which can be drawn in. The needle cannula then being able to be drawn in when the piston is drawn in at the end of a stroke. The handling is a disadvantage of the known syringe. For example, the needle cannula has to be installed in a complicated manner at the hollow body, with the needle cannula being able to be contaminated by bacteria, etc. Moreover, a fluid has to be drawn into the syringe in a manner complicated for the user.

SUMMARY

It is therefore an object of the present invention to provide a syringe which can be operated as simply as possible.

This object is satisfied by a syringe having the features described herein.

Further developments of the invention result from the description and from the drawings.

In accordance with the invention, a syringe is proposed which comprises a hollow body, a piston and an intermediate piece. The hollow body has a surrounding hollow body surface and forms a passage therein. An axis is formed in an axial longitudinal direction of the hollow body. The passage has a rear body opening and a front body opening which are arranged opposite to one another in the longitudinal direction. A first needle seat is formed at the front body opening, in which needle seat a needle cannula is arranged and relative to which needle seat the needle cannula is movable along the axis. The piston is arranged in the hollow body and is movable in the passage along the axis, wherein the piston comprises a front piston opening, a rear piston end and a surrounding intermediate wall. The intermediate wall is arranged between the front piston opening and the rear piston end and forms a receiving chamber for receiving at least one fluid. The intermediate piece is arranged in the receiving chamber and is movable along the axis, wherein a first sealing region, which seals the receiving chamber in a storage position, acts between the intermediate wall and the intermediate piece. A second needle seat and a supply space, which is in particular formed as a channel or in the manner of a channel, are formed in the intermediate piece, with the second needle seat and the supply space being in flow communication with one another. The piston, the hollow body and the intermediate piece are movable into a release position by a coaxial relative movement starting from the storage position. A seal is provided in the storage position between the supply space and the receiving chamber, said seal being able to be cancelled by the coaxial relative movement such that the receiving chamber and the supply space are in flow communication in the release position.

The syringe can, for example, be a disposable syringe for single use. Plastic, in particular PP or COC, can, for example, be a material from which the syringe is manufactured. Possible materials are also PE, PA, PBT and PMMA. The material can, however, also be glass, a metal alloy or metal. The material can advantageously be a pressure-resistant material.

The hollow body can be a tubular hollow body, preferably, but not necessarily, having a circular, ellipsoidal or polygonal base surface. The hollow body has a surrounding hollow body surface which forms a passage therein. An axis is formed in an axial longitudinal direction of the hollow body, preferably through the centroid of the two base surfaces of the hollow body. The hollow body can be configured as a mainly hollow cylindrical tube, with the passage having a rear body opening and a front body opening which are arranged opposite one another in the longitudinal direction.

A first needle seat is formed at the front body opening, with a needle cannula being arranged in the first needle seat and the needle cannula being movable along the axis. The front body opening can be of nozzle shape, for example. The first needle seat can be configured with a tubular form into the hollow body with a needle seat opening. The first needle seat can preferably, but not necessarily, have a circular, ellipsoidal or polygonal base surface. The first needle seat can be aligned along the axis. A fluid can flow out of the receiving chamber in the needle cannula, in particular a first fluid and a second fluid can flow out of the receiving chamber after one another. In the storage position, the needle cannula can be arranged in a first needle seat such that the needle cannula is completely moved into the hollow body. In the release position, the needle cannula can be moved out of the first needle seat, that is out of the hollow body, with the needle cannula being able to be held in the intermediate piece. In a drawn in position, the needle cannula can be moved completely into the hollow body and can no longer be arranged in the first needle seat.

The piston is arranged in the hollow body, in particular in the passage, and is movable along the axis. The piston comprises a front piston opening, which is arranged in the direction of the front body opening, and a rear, in particular closed, piston end. The front piston opening and the rear piston end are arranged opposite one another in the longitudinal direction. The piston can be moved from the storage position into the release position and vice versa. The piston can additionally in particular be moved into a flushing position and into a drawn in position, with the flushing position being located between the release position and the drawn in position. A movement of the piston from the storage position into the release position can take place, for example, as with a conventional syringe, by pressing onto the rear piston end which can be configured as a push button, for example. So that the piston cannot be pressed further into the hollow body in the release position, the rear piston end can be configured as an abutment device, for example as a projection. In the storage position, the piston can be held in the hollow body by a holding device, i.e. a movement of the piston can be prevented, and indeed such that a movement of the piston is only possible from a specific force action onto the rear piston opening onward. The holding device can, for example, comprise a dimple in the piston and a groove in the hollow body, or vice versa. The dimple can be latched in the groove, for example. The piston can also be guided in the axial direction by a guide element in the passage.

The piston equally comprises a surrounding intermediate wall which is arranged between the front piston opening and the rear piston end and which forms a receiving chamber for receiving fluid, in particular a first fluid and a second fluid. The receiving chamber can be configured as a U-shaped tube, with the base surface of the receiving chamber being able to have a circular, ellipsoidal or polygonal base surface. The receiving chamber can in particular have a volume of 0.1 to 100 ml, preferably a volume of 0.5 to 2 ml.

A second needle seat is formed in the intermediate piece which is arranged in the receiving chamber and which is movable along the axis, with the needle cannula being arranged in the second needle seat and being movable along the axis. The needle cannula can, however, also be held in the intermediate piece, in particular in an inner element or in the second needle seat, such that a coaxial movement of the needle cannula independently of the intermediate piece is not possible. The second needle seat can be aligned along the axis. In the storage position, the needle cannula can be arranged in the first and second needle seats so that the needle cannula is moved at least approximately completely into the hollow body. In the release position, the needle cannula can be moved out of the hollow body, with the needle cannula being held firmly in the axial direction, for example, by a needle holder in the intermediate piece, in particular by a needle holder in the second needle seat. The needle cannula can e.g. be latched to the needle holder or can be bonded or clamped into the needle holder. The intermediate piece can be moved in the passage along the axis by a force transmission from the piston onto the intermediate piece.

In accordance with the invention, a supply space is formed in the intermediate piece and the supply space is in flow communication with the second needle seat. The supply space can be provided in the form of one or more bores in the intermediate piece. The bore can e.g. have a largest diameter of 3 mm and can, for example, be cylindrical. A cross-sectional shape of the bore perpendicular to or in parallel with the axis can e.g. be rectangular or generally polygonal. The supply space can be arranged with a longitudinal axis at an angle of e.g. 50 to 90 degrees, preferably of at least approximately 90 degrees, to the axis. Flow communication is in particular to be understood such that a fluid can flow or stream from the supply space into the second needle seat and into the needle cannula.

The piston, the hollow body and the intermediate piece are movable relative to one another by a coaxial movement starting from a storage position into a release position. In the storage position, the receiving chamber is sealed with respect to the supply space. The storage position is in particular to be understood such that the piston can be pulled out of the hollow body, such that the front piston opening is therefore located in the vicinity of the rear body opening, and such that it is prevented by sealing that a fluid flows from the receiving chamber into the intermediate piece and from there into the needle cannula. The release position is to be understood such that the piston has been moved by a coaxial movement into the hollow body, for example by pressing at the rear piston end, and such that the seal is thereby cancelled so that the fluid can flow from the receiving chamber into the intermediate piece and from there into the needle cannula. In this respect, starting from the storage position, the needle cannula can first be moved out, with the seal still remaining activated. The seal is deactivated on the transition into the release position. In a subsequent drawn in position with a piston pulled back again, the needle cannula can moreover be drawn into the hollow body.

The advantages of the syringe in accordance with the invention are that the syringe serves as a functional, a primary packaging means or device and an active ingredient is already present in the syringe and does not first have to be drawn in, whereby, for example, contamination problems can be precluded. In addition, the syringe is easier to operate, for example with one hand, because a complex plugging on or screwing on of the needle cannula is dispensed with. The optionally provided draw-in position has the advantage that a risk of injury or infection by the needle cannula can be precluded after the use of the syringe.

In a possible embodiment of the invention, the intermediate piece comprises an outer element and an inner element. The inner element in this respect comprises the second needle seat and an abutment for the outer element. The inner element is in particular arranged with the abutment such that an axial movement of the inner element relative to the outer element is bounded by the abutment in the direction of the rear body end. The supply space can be of conical design. A seal can be formed between the inner element and the outer element.

The intermediate piece can be in one part or in multiple parts. The intermediate piece can comprise an outer element and an inner element, with the second needle seat being able to be arranged either at the outer element or at the inner element. The inner element can be arranged partly, or also completely, in the outer element. The inner element can in particular be arranged in a bore which can have a circular or polygonal cross-section. The supply space can be arranged at the inner element or at the outer element. The inner element further comprises an abutment for the outer element. The abutment can be configured, for example, as a peripheral edge, in the form of one or more webs or as a step. In the storage position, a first sealing region can be formed between the intermediate wall and the outer element of the intermediate piece and a second sealing region can be formed between the inner element and the outer element. The first sealing region can be formed as a seal, for example as a groove at the intermediate wall of the receiving chamber and as a dimple at the intermediate piece, in particular at the outer element, or vice versa. The second sealing region can likewise be formed as a seal, for example as a groove at the outer element and as a dimple at the inner element. The first sealing region and/or the second sealing region can alternatively be formed as an O-ring seal. The first sealing region and/or the second sealing region can comprise one or more seals. The active ingredient can thus advantageously already be stored in the syringe and a simplified release principle of the active ingredient can be achieved.

In a possible embodiment of the invention, the receiving chamber is divided by a separating element into a first chamber and a second chamber. In a flushing position, the second chamber and the supply space can be in flow communication. In the storage position, a sealing region is formed and arranged between the intermediate wall and the separating element such that the second chamber and the supply space have no flow communication. The separating element can be configured as a film or as a plug which is arranged movably along the axis in the receiving chamber. The intermediate piece, on a multi-part embodiment of the intermediate piece e.g. an inner element of the intermediate piece, can be formed as a mandrel in the direction of the rear body end to break open the separating element.

The receiving chamber can be divided by a separating element into exactly two chambers, namely a first chamber and a second chamber. The receiving chamber can, however, also be divided into more than two chambers which are separated by a plurality of separating elements and which can receive more than two fluids in total. Each separating element can be configured as a film or as a plug.

In general, the or each separating element can be formed from plastic or from a metal material. The separating element is respectively arranged in the receiving chamber such that the respective chambers are separated in a fluid-tight manner. If a first chamber and a second chamber are provided, they can receive two fluids, with a first fluid being able to be arranged in the first chamber and a second fluid being able to be arranged in the second chamber. In addition, in the storage position or in the release position, a sealing region can be formed and arranged between the intermediate wall and the separating element such that the second chamber and the supply space as well as the second chamber and the first chamber do not have any flow communication. This sealing region can be configured as a seal, for example as a groove in the intermediate wall and as a dimple complementary thereto in the separating element, or vice versa. The sealing region can, however, also be an O ring. The sealing region can comprise one or more seals. A flushing position is to be understood such that the second chamber and the supply space are in flow communication with one another. The separating element or its position can be mechanically changed to establish this flow communication. For example, the film can be pierced by the mandrel or the sealing region between the separating element and the intermediate wall can be deactivated so that the second chamber and the supply space are in flow communication. In the storage position and/or in the release position, in contrast, the separating element separates the second chamber and the first chamber as well as the second chamber and the supply space such that they have no flow communication. The first fluid can in this respect, for example, be a medicine to be dispensed and the second fluid can be a flushing solution. It is of advantage in this respect that the first fluid and the second fluid, but also more than two fluids, can thus be functionally separated. In addition, the handling and the operation of the syringe is simpler since the active ingredient is already contained in the syringe and no longer has to be drawn up into the syringe.

In a possible embodiment of the invention, the inner element of the intermediate piece is configured as a further hollow body, with the piston being arranged movably in the further hollow body. The further hollow body can be a tubular hollow body, preferably, but not necessarily, having a circular, ellipsoidal or polygonal base surface. The shape of the further hollow body can correspond to that of the hollow body, with the further hollow body being able to be arranged in the passage of the hollow body. The further hollow body can comprise a further passage and extend along the axis. The further hollow body can be configured as a hollow cylindrical tube. The piston can furthermore be arranged in the further hollow body. The coaxial movement of the piston can take place along the axis in the further hollow body which in turn moves along the axis in the hollow body. A better support and guide stability of the intermediate piece is thus advantageously established.

In a possible embodiment of the invention, a spring is arranged in the passage against whose restoring force the piston is movable in the direction of the front body opening of the hollow body. The needle cannula can advantageously be more easily drawn into the hollow body by the spring, i.e. the spring can ensure that the syringe moves into the draw-in position or the spring can assist the transition into the draw-in position.

In a further possible embodiment of the invention, a means or device is provided for an automatic lateral pivoting or deflecting of the intermediate piece in an end position and/or draw-in position. The device is in particular active between a rear end of the receiving chamber and a rear end of the intermediate piece and in particular comprises a sloping surface. It is possible by such device to act on the needle cannula via the intermediate piece and the second needle seat by a pivot force or deflection force which endeavors to move the needle cannula from a working alignment in parallel with the longitudinal axis of the hollow body into a safety alignment inclined with respect to the longitudinal axis. The needle cannula can in particular adopt the inclined position as soon as it moves out of engagement with the first needle seat which is formed at the front body opening and which otherwise also ensures the working alignment of the needle cannula against the action of the pivot force or deflection force.

The invention further relates to a syringe as described herein, wherein the receiving chamber already contains at least one fluid, in particular a liquid containing at least one medicine to be dispensed, wherein in particular the receiving chamber contains a liquid containing at least one medicine to be dispensed in a first chamber of the receiving chamber and a flushing solution in a second chamber of the receiving chamber.

The invention furthermore relates to a use of a syringe as described herein for discharging a fluid already contained in the receiving chamber without drawing up the fluid, in particular for injecting a liquid containing at least one medicine to be dispensed (administered), wherein a liquid containing at least one medicine to be dispensed is discharged from a first chamber of the receiving chamber in a first phase and subsequently a flushing solution is discharged from a second chamber of the receiving chamber in a second phase.

Further advantages, features and details of the invention result with reference to the following description of embodiments and with reference to the drawing in which elements which are the same or have the same function are provided with identical reference numerals. The skilled person will also expediently consider the features individually and combine them to further sensible combinations.

BRIEF DESCRIPTION OF THE DRAWINGS

The invention will be explained in more detail hereinafter with reference to the drawings.

DETAILED DESCRIPTION OF THE EMBODIMENTS

Figure 1:
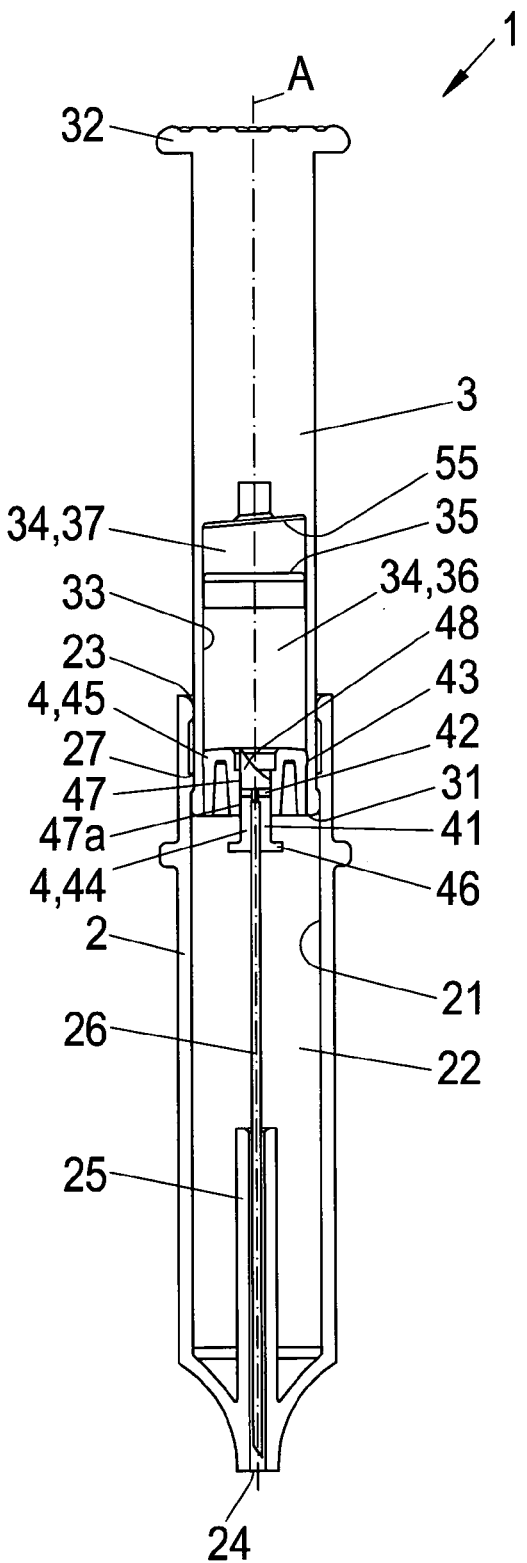
FIG. 1 is a schematic representation of a first embodiment of a syringe in accordance with the invention in a storage position.

FIG. 1 shows a schematic representation of a first embodiment of a syringe 1 in accordance with the invention in a storage position. The syringe 1 comprises a hollow body 2, a piston 3 and an intermediate piece 4. The hollow body has a surrounding hollow body surface 21 and a passage 22 therein. The hollow body 21 has a circular base surface and forms a cylindrical passage 22. An axis A is formed in an axial longitudinal direction of the hollow body 2. The passage 22 moreover has a rear body opening 23 and a front body opening 24 which are arranged opposite one another in the longitudinal direction.

A first tubular needle seat 25 is formed at the front body opening 24 so that the front body opening 24 is closed except for a needle seat opening in the first needle seat 25. A needle cannula 26 is arranged in the first needle seat 25 and is movable relative to the first needle seat 25 along the axis A.

The piston 3 is arranged in the hollow body 2 and is movable in the passage 22 along the axis A. The piston 3 further comprises a front piston opening 31, which is arranged in the direction of the front body opening 24, and a rear, closed piston end 32. The front piston opening 31 and the rear piston end 32 are arranged opposite one another along the axis A in the longitudinal direction.

A surrounding intermediate wall 33, which forms a receiving chamber 34 for receiving fluid, is arranged between the front piston opening 31 and the rear piston end 32. The receiving chamber 34 is divided by a separating element 35 into a first chamber 36 and into a second chamber 37. The separating element 35 is formed as a film. The chambers 36, 37 can each receive a fluid, with a first fluid being arranged in the first chamber 36 and a second fluid being arranged in the second chamber 37. In the storage position, the film separates the second chamber 37 from the first chamber 36 and thus from a supply space 42 formed in the intermediate piece 4 such that they do not have any flow communication.

The first fluid can in this respect, for example, be a medicine to be dispensed and the second fluid can be a flushing solution.

The intermediate piece 4 is movably arranged in the passage 22 along the axis A. A second needle seat 41 is formed in the intermediate piece 4, with the needle cannula 26 being firmly held in the second needle seat 41. The intermediate piece 4 is in two parts and comprises an outer element 45 and an inner element 44, wherein the second needle seat 41 is formed at the inner element 44. The inner element 44 further comprises an abutment 46 for the outer element 45, the abutment being formed as a peripheral shoulder. The abutment 46 is arranged in the direction of the front body opening 24 and acts as a stopper for the outer element 45 which can therefore stop a movement of the outer element 45. In addition, the inner element 44 is formed in the direction of the rear body opening 23 as a mandrel 48 to break open the separating element 35. The intermediate piece 4 furthermore has the supply space 42 which is formed in the intermediate piece 4 and which can in particular be of conical design. The second needle seat 41 and the supply space 42 are in flow communication so that the first fluid and the second fluid can flow via the supply space 42 into the needle cannula 26 when seals acting in the storage position are deactivated.

The piston 3, the hollow body 2 and the intermediate piece 4 are movable by m a coaxial relative movement starting from a storage position into a release position. In the storage position present in FIG. 1, a first sealing region 43 is formed between the intermediate wall 33 and the outer element 45 of the intermediate piece 4 and a second sealing region forming further seals 47, 47a is formed between the inner and outer elements 44, 45, wherein, viewed in the axial direction, a seal 47 is disposed in front of the supply space 42 and a seal 47a is disposed behind the supply space 42. The first sealing region 43 comprises a groove at the intermediate wall 33 of the receiving chamber 34 and a dimple at the intermediate piece 4 or at the outer element 45. The second sealing region 47, 47a in each case comprises a further groove at the outer element 45 and a dimple at the inner element 44.

The first sealing region 43 prevents fluid from being able to flow out of the receiving chamber 34 into the passage 22 of the hollow body 2. The second sealing region prevents fluid from being able to flow into the supply space 42 by the seal 47 in the storage position, on the one hand, and from fluid being able to flow through between the inner element 44 and the outer element 45 into the passage 22 of the hollow body 2 by the seal 47a, on the other hand. The receiving chamber 34 and the supply space 42 are thus not in flow communication in the storage position. Neither the first fluid nor the second fluid therefore flow from the receiving chamber 34 into the supply space 42.

The receiving chamber 34 is bounded at the rear end by a sloping surface 55 which cooperates with the rear end of the intermediate piece 4, which will be looked at in more detail in the following in connection with FIGS. 3 and 4.

Figure 2:
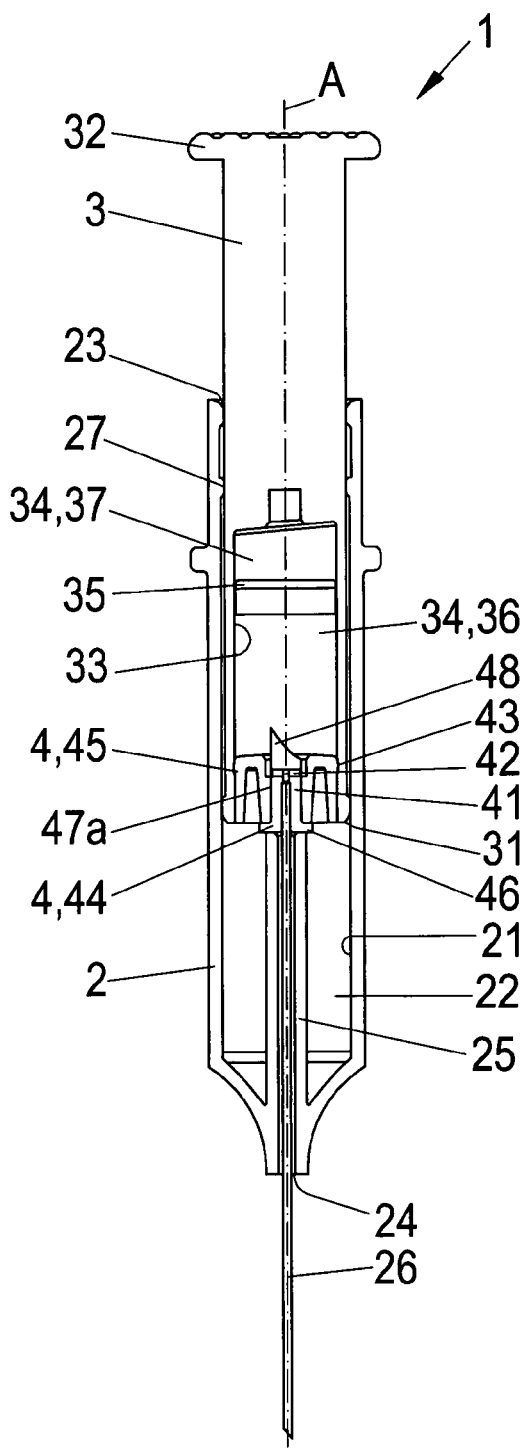
FIG. 2 is a schematic representation of the first embodiment in the release position.

A schematic representation of the first embodiment in the release position is shown in FIG. 2. The release position corresponds to an activated position, i.e. the piston 3 has been moved along the axis A in the passage 22 in the direction of the front body opening 24 by a coaxial movement by a force transmission, for example by pressure onto the rear piston end 32. In this respect, a holding device 27 is provided in the form of a peripheral, inwardly projecting rib which holds the piston 3 at the hollow body surface 21 in that a friction force is generated which has to be overcome by the force transmission.

In the release position, the inner element 44 has been moved along the axis A in the direction of the front body opening 24 and is arranged at the first needle seat 25. In this respect, the inner element 44 lies on the first needle seat 25 and the first and second needle seats 25, 41 together form an approximately continuous needle seat. In this respect, the needle cannula 26, which is arranged in the storage position completely in the first and second needle seats 25, 41 and in the hollow body 2, has been moved along the axis A through the front body opening 24 out of the hollow body 2 and is located partly outside the hollow body 2. The outer element 45 has likewise been moved along the axis A in the direction of the front body opening 24 and is arranged at the abutment 46, whereby the sealing effect of the seal 47 of the second sealing region has been deactivated so that, in the release position, the first chamber 36 of the receiving chamber 34 and the supply space 42 are in flow communication.

In the release position, the first fluid can flow from the first chamber 36 through the supply space 42 into the inner element 44 or into a needle seat opening formed therein and can then flow into the needle cannula 26.

On the subsequent transition into a flushing position (not shown) after emptying the first chamber 36, the mandrel 48 pierces the film, whereupon the second chamber 37 and the supply space 42 are in flow communication and a flushing procedure can be carried out by discharging the second fluid, that is by emptying the second chamber 37, through the needle cannula 26.

Figure 3:
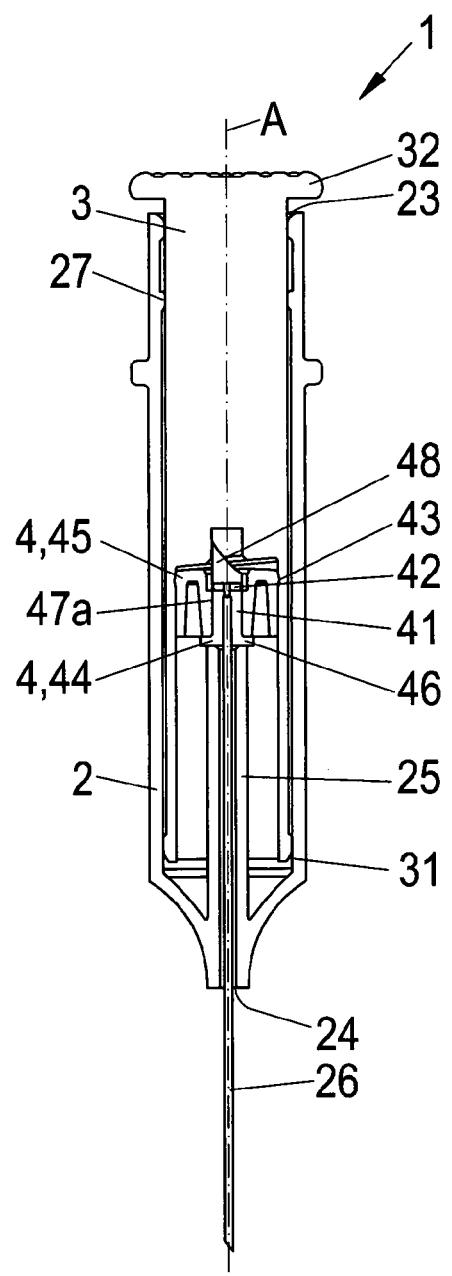
FIG. 3 is a schematic representation of the first embodiment in an end position after discharging the first fluid and the second fluid.

FIG. 3 shows a schematic representation of the first embodiment after discharging the first fluid and the second fluid. In this end position, the piston 3 contacts the intermediate piece 4 with the slope 55 formed at the rear end of the receiving chamber 34 while interposing the pierced film 35. The piston 3 is arranged approximately completely in the passage 22 of the hollow body 2, with a further movement of the piston 3 being prevented along the axis A in the direction of the front body opening 24. The separating element 35 has been broken open by the mandrel 48 and the second fluid has flowed from the second chamber 37 (FIG. 2) via the supply space 42 into the needle cannula 26. A recess into which the mandrel 48 projects is disposed in an axial direction to the rear beyond the slope 55.

The slope 55 endeavors to locate the intermediate piece 4 together with the inner element 44 and the needle cannula 26 in a slanted position, which is, however, not possible in the position in accordance with FIG. 3 since the needle cannula 26 is still located in the first needle seat 25 and can thus not be deflected or pivoted.

Figure 4:
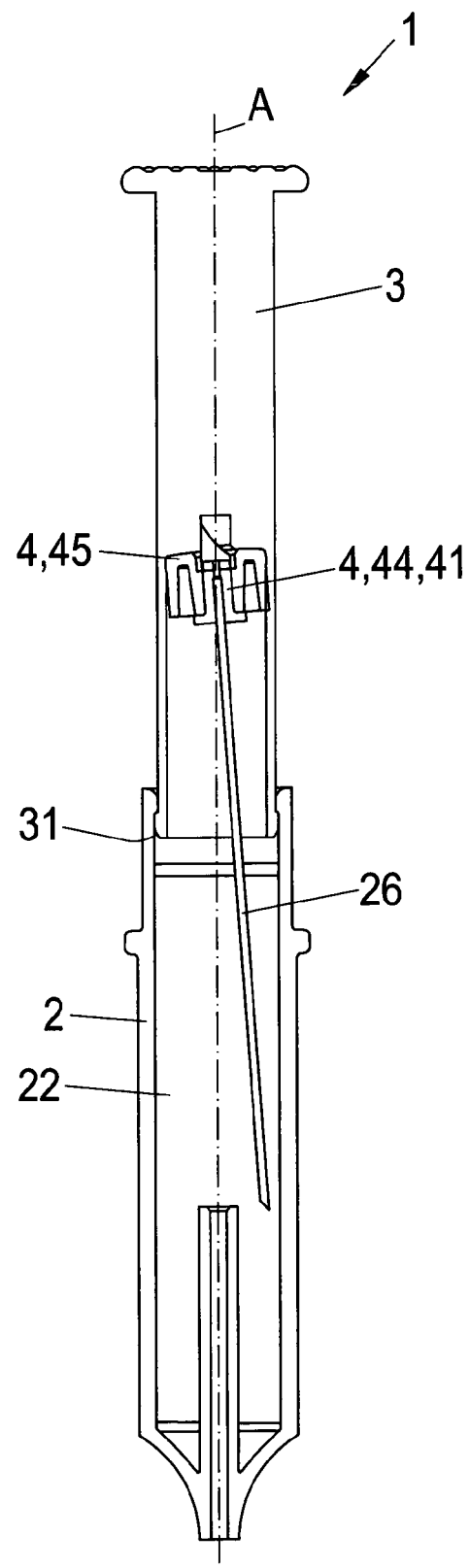
FIG. 4 is a schematic representation of the first embodiment in a draw-in position.

FIG. 4 shows a schematic representation of the first embodiment in a draw-in position. In the draw-in position, the piston 3 has been withdrawn approximately completely out of the passage 22 of the hollow body 2, with the front piston opening 31 being arranged in the passage 22. The needle cannula 26 is held firmly at the intermediate piece 4 via the inner element 44 at the second needle seat 41 such that the needle cannula 26 is taken along on the backward movement of the piston 3. In this respect, the needle cannula 26 is completely pulled into the passage 22 and out of the first needle seat 25 and is thus released. The intermediate piece 4, pre-biased into a corresponding sloping position due to the slope 55, can adopt the sloping position by this release of the needle cannula 26 and can consequently locate the needle cannula 26 in a slanted position which can thus not accidentally or randomly thread back into the first needle seat 25 and is consequently so-to-say captured in the hollow body 2. The needle cannula 26 or the syringe 1 can therefore not be reused and there is no risk of injury.

Figure 5:
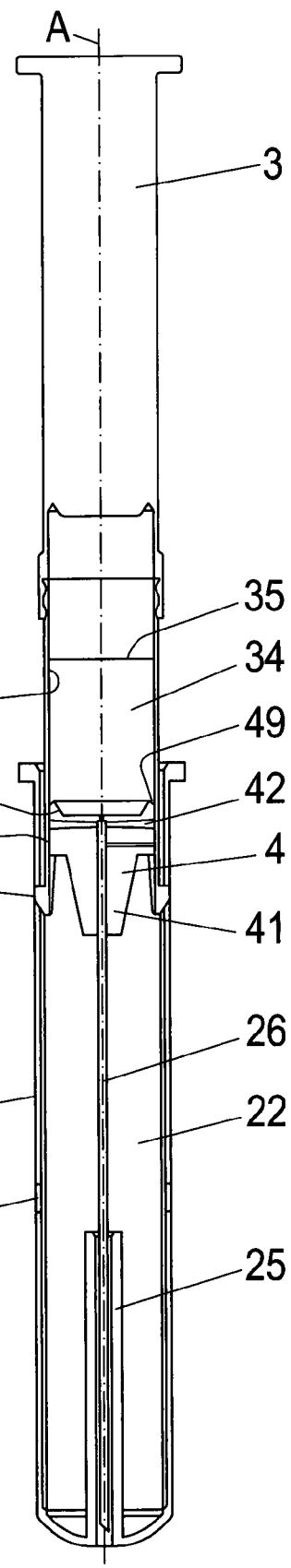
FIG. 5 is a schematic representation of a second embodiment in the storage position.

FIG. 5 shows a schematic representation of a second embodiment of a syringe in accordance with the invention in the storage position. The design of the syringe 1 in this respect has a number of common features with the syringe 1 from FIGS. 1 to 4 so that substantially the differences will be looked at.

The intermediate piece 4 is arranged, analog to FIGS. 1 to 4, movably in the passage 22 along the axis A. A second needle seat 41 is formed in the intermediate piece 4, with the needle cannula 26 being firmly held in the second needle seat 41. The intermediate piece 4 is in one part, unlike the embodiment in accordance with FIGS. 1 to 4. The single-part intermediate piece 4 has a supply space 42 which is formed in the intermediate piece 4. In the storage position shown in FIG. 5, the first sealing region 43a is formed between the intermediate wall 33 and the intermediate piece 4 and forms a first seal at the rear side of the supply space 42. A second seal 43b is arranged at the front side of the supply space 42. The seal formed by the first sealing region 43a comprises a groove at the intermediate wall 33 of the receiving chamber 34 and a dimple at the intermediate piece 4. The first sealing region 43a prevents fluid from being able to flow into the supply space 42 in the storage position, whereas the second seal 43b prevents fluid from being able to flow from the supply space 42 into the passage 22 of the hollow body 2. The receiving chamber 34 and the supply space 42 are thus not in flow communication in the storage position, i.e. neither the first fluid nor the second fluid flows from the receiving chamber 34 into the supply space 42.

In the storage position, the piston 3 is held by a holding device 27 and can only be moved by a force transmission. In an active position, not shown, the piston 3 is held by an activating device 28 and can only be moved into the release position by a force transmission. The needle cannula 26 is moved out in the active position. The separating element 35 only shown schematically here is broken open in this second embodiment by a sharp peripheral edge 49 of the intermediate piece 4. A slope can be provided in accordance with the embodiment of FIGS. 1 to 4 or another means or device can be provided for pivoting or deflecting the needle cannula 26.

Figure 6:
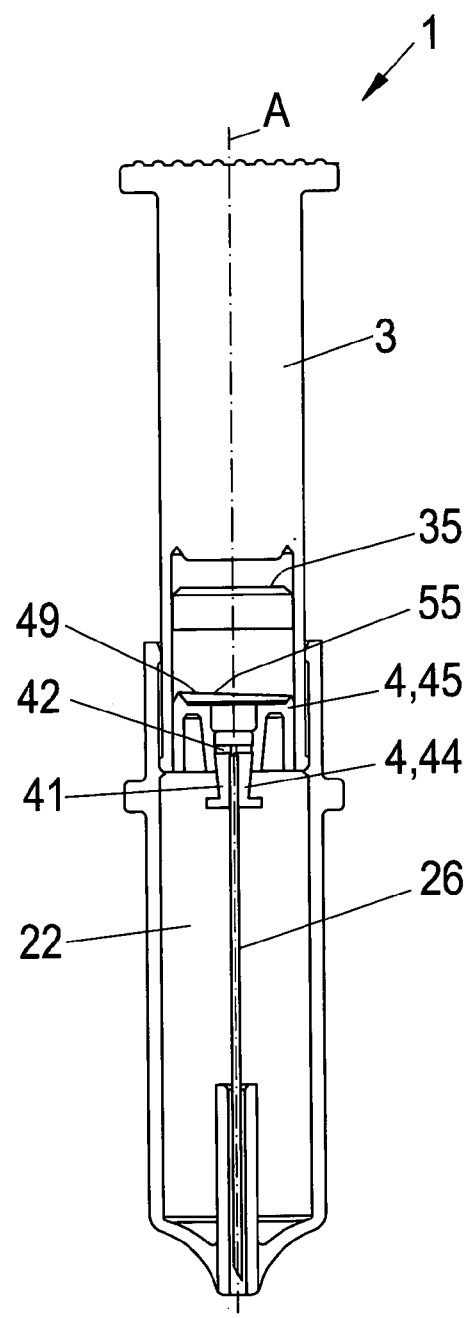
FIG. 6 is a schematic representation of a third embodiment in the storage position.

FIG. 6 shows a schematic representation of a third embodiment of a syringe in accordance with the invention in the storage position. The design of the syringe 1 in this respect has a number of common features with the syringe 1 from FIGS. 1 to 4 so that substantially the differences will be looked at. The two-part intermediate piece 4 is movably arranged in the passage 22 along the axis A. A second needle seat 41 is formed in the intermediate piece 4, with the needle cannula 26 being firmly held in the second needle seat 41. A sharp peripheral edge 49 for breaking open the separating element 35 is formed at the outer element 45, in the direction of the rear piston end 32. The edge 49 does not have a peripherally constant height, but rather defines a plane 55 which is inclined with respect to the axis A and which, analog to the sloping surface 55 in the embodiment of FIGS. 1 to 4, ensures a slanted position of the needle cannula 26 in the draw-in position.

Figure 7:
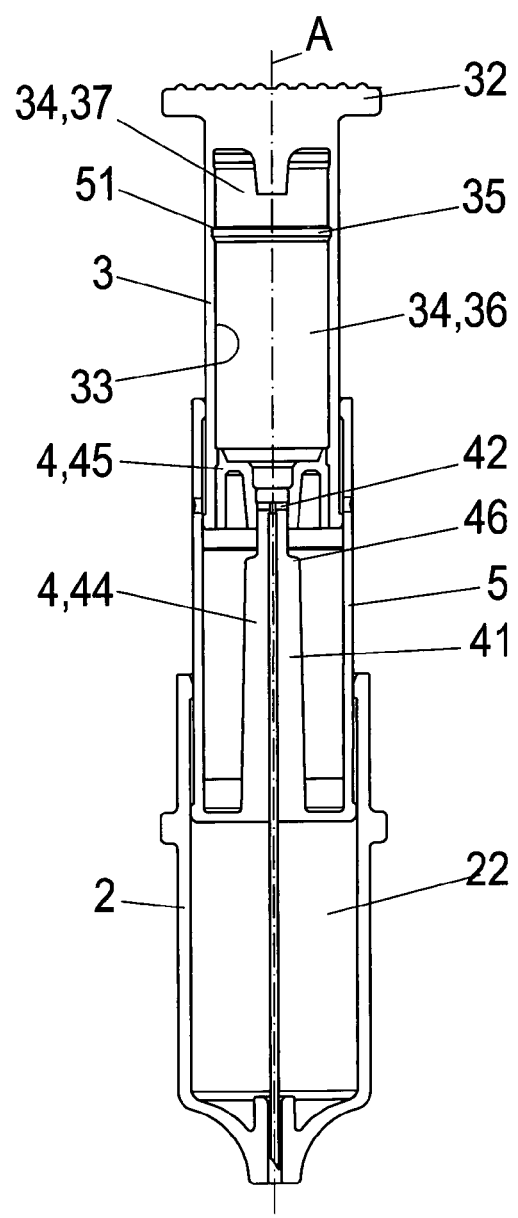
FIG. 7 is a schematic representation of a fourth embodiment in the storage position.

FIG. 7 shows a schematic representation of a fourth embodiment of a syringe in accordance with the invention in the storage position. The design of the syringe 1 substantially corresponds to the syringe 1 from FIGS. 1 to 4 so that substantially the differences will be looked at. The intermediate piece 4 is in two parts, with the inner element 44 being configured such that the second needle seat 41 is hollow cylindrical and has two different outer diameters and so forms the abutment 46 for the outer element 45. In addition, the inner element 44 is formed as a further hollow body 5 in which the piston 3 is arranged. The inner element 44, which is configured in one piece overall, consequently comprises the radially inwardly disposed needle seat 41 and an outer part which defines the hollow body 5, which is arranged concentrically to the needle seat 41 and which receives the piston 3. The inner element 44 has no mandrel 48.

The further hollow body 5 is arranged in the passage 22 of the hollow body 2. The coaxial relative movement of the piston 3 thus takes place along the axis A in the further hollow body 5 of the inner element 44 which in turn moves along the axis A in the hollow body 2.

The separating element 35 is configured as a plug and is arranged in the receiving chamber 34 movably along the axis A. The separating element 35 can be displaced by the outer element 45 of the intermediate piece 4 to empty the second chamber 37. Provision can alternatively be made that the separating element 35, which is e.g. formed as a film, is broken open by the outer element 45, in particular by a sharp edge formed at the outer element 45.

In addition, a sealing region 51 which acts in the storage position or the release position is configured and arranged between the intermediate wall 33 and the separating element 35 such that the second chamber 37 and the supply space 42 do not have any flow communication, just as the second chamber 37 and the first chamber 36 have no flow communication. The sealing region 51 comprises a groove in the intermediate wall 33 and a dimple complementary thereto in the separating element 35. In the flushing position, the sealing region 51 is deactivated and the second chamber 37 and the supply space 42 are in flow communication.

Figure 8:
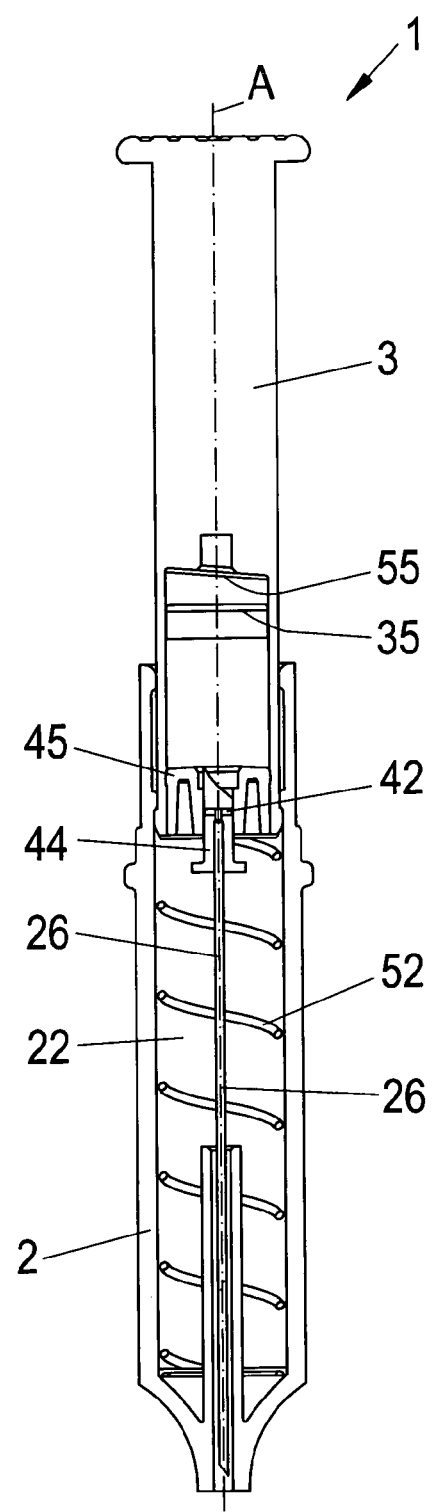
FIG. 8 is a schematic representation of a fifth embodiment in the storage position.

FIG. 8 shows a schematic representation of a fifth embodiment of a syringe 1 in accordance with the invention in the storage position. The design of the syringe 1 substantially corresponds to the syringe 1 from FIGS. 1 to 4 so that substantially the differences will be looked at. To ensure that, on the transition into the draw-in position, the needle cannula 26 is drawn completely into the passage 22, a spring 52 is arranged in the passage 22 against whose restoring force the piston 3 has to be pressed to the front, starting from the storage position. The spring 52 consequently effects or assists the transition into the draw-in position in accordance with the proper use of the syringe 1.

The invention claimed is:

1. A syringe comprising:
    a hollow body having a surrounding hollow body surface and forming a passage therein, an axis being formed in an axial longitudinal direction of the hollow body and the passage having a rear body opening and a front body opening, which are arranged opposite to one another in the axial longitudinal direction, a first needle seat being formed at the front body opening, the first needle seat having a needle cannula arranged therein, the needle cannula being movable along the axis relative to the first needle seat;
    a piston arranged in the hollow body and being movable in the passage along the axis, the piston comprising a front piston opening, a rear piston end and a surrounding intermediate wall arranged between the front piston opening and the rear piston end and which forms a receiving chamber for receiving at least one fluid; and
    an intermediate piece arranged in the receiving chamber and being movable along the axis, a first sealing region sealing the receiving chamber in a storage position acting between the intermediate wall and the intermediate piece,
    a second needle seat and a supply space being formed in the intermediate piece, with the second needle seat and the supply space being in flow communication,
    the piston, the hollow body and the intermediate piece being movable into a release position by a coaxial relative movement starting from the storage position, and
    a seal being disposed in the storage position between the supply space and the receiving chamber, the seal being able to be cancelled by the coaxial relative movement of the piston relative to the hollow body such that the receiving chamber and the supply space are in flow communication in the release position.

2. The syringe in accordance with claim 1, wherein the intermediate piece comprises an outer element and an inner element and the inner element is movable axially relative to the outer element to cancel the seal.

3. The syringe in accordance with claim 2, wherein the inner element comprises an abutment for the outer element.

4. The syringe in accordance with claim 3, wherein the inner element is arranged such that an axial movement of the inner element relative to the outer element is bounded by the abutment in the direction of the rear body end.

5. The syringe in accordance with claim 2, wherein the seal is formed between the inner element and the outer element.

6. The syringe in accordance with claim 2, wherein the inner element forms a further hollow body, and the piston is arranged movable in the further hollow body.

7. The syringe in accordance with claim 2, wherein the inner element comprises the second needle seat.

8. The syringe in accordance with claim 1, wherein the receiving chamber is divided by a separating element into a first chamber and a second chamber, the first chamber being disposed between the second chamber and the intermediate piece.

9. The syringe in accordance with claim 8, wherein a second sealing region is formed and arranged in the storage position between the intermediate wall and the separating element such that the second chamber and the supply space do not have any flow communication.

10. The syringe in accordance with claim 8, wherein the separating element is a film.

11. The syringe in accordance with claim 8, wherein the intermediate piece is formed as a mandrel in the direction of the rear body opening to break open the separating element.

12. The syringe in accordance with claim 8, wherein the separating element is a plug and is arranged movable along the axis in the receiving chamber.

13. The syringe in accordance with claim 8, wherein the second chamber and the supply space are in flow communication in a flushing position.

14. The syringe in accordance with claim 1, wherein the intermediate piece is configured in one part and is movable axially relative to the piston for cancelling the seal.

15. The syringe in accordance with claim 1, further comprising a spring having a restoring force, and the piston is movable against the restoring force of the spring in the direction of the front body opening of the hollow body, the spring being arranged in the passage.

16. The syringe in accordance with claim 1, wherein the receiving chamber contains at least one fluid in a first chamber of the receiving chamber and a flushing solution in a second chamber of the receiving chamber.

17. The syringe in accordance with claim 16, wherein the at least one fluid is a liquid containing at least one medicine to be dispensed.

18. The syringe in accordance with claim 1, further comprising a device configured to automatically laterally pivot or deflect the intermediate piece disposed in an end position.

19. The syringe in accordance with claim 18, wherein the device is configured to act between a rear end of the receiving chamber and the intermediate piece.

20. The syringe in accordance with claim 18, wherein the device comprises at least one sloping surface or defines at least one inclined plane.

21. A method comprising:
    operating a syringe in accordance with claim 1 for discharging a fluid already contained in the receiving chamber without drawing in the fluid.

22. The method in accordance with claim 21, wherein the fluid is a liquid and the liquid contains at least one medicine to be dispensed, the liquid being discharged from a first chamber of the receiving chamber in a first phase and subsequently a flushing solution is discharged from a second chamber of the receiving chamber in a second phase.

* * * * *